United States Patent [19]

Sham et al.

[11] Patent Number: 5,256,677
[45] Date of Patent: Oct. 26, 1993

[54] RETROVIRAL PROTEASE INHIBITING COMPOUNDS

[75] Inventors: Hing L. Sham, Gurnee; Daniel W. Norbeck, Lindenhurst; Dale J. Kempf, Libertyville; Chen Zhao, Gurnee, all of Ill.

[73] Assignee: Abbott Laboratories, Abbott Park, Ill.

[21] Appl. No.: 901,057

[22] Filed: Jun. 19, 1992

Related U.S. Application Data

[60] Division of Ser. No. 675,780, Mar. 27, 1991, Pat. No. 5,151,438, which is a continuation-in-part of Ser. No. 518,730, May 9, 1990, Pat. No. 5,142,056, which is a continuation-in-part of Ser. No. 456,124, Dec. 22, 1989, abandoned, which is a continuation-in-part of Ser. No. 405,604, Sep. 8, 1989, abandoned, which is a continuation-in-part of Ser. No. 355,945, May 23, 1989, abandoned.

[51] Int. Cl.$^5$ .................. A61K 31/44; C07D 213/30
[52] U.S. Cl. .................. 514/351; 514/352; 514/357; 514/616; 546/337; 546/331; 546/332; 546/300; 546/335; 546/301; 546/309; 546/312
[58] Field of Search ............ 546/337, 331, 332, 300, 546/335, 301, 309, 312; 514/351, 352, 357, 616

[56] References Cited

PUBLICATIONS

Zeffren et al. The Study of Enzyme Mechanism p. 87, 1974.
Wade, J. R. Organic Chemistry 1987 ... p. 349.
Merck Index. 11th Edition. pp. 1282–1283 1869.

Primary Examiner—Jane T. Fan
Attorney, Agent, or Firm—Steven R. Crowley

[57] ABSTRACT

Compounds are disclosed which are retroviral protease inhibitors. Also disclosed are methods of using the compounds and compositions for inhibiting a retroviral protease and for treating an HIV infection.

13 Claims, No Drawings

RETROVIRAL PROTEASE INHIBITING COMPOUNDS

This invention was made with Government support under contract number AI27220-01 awarded by the National Institute of Allergy and Infectious Diseases. The Government has certain rights in this invention.

This is a division of U.S. patent application Ser. No. 675,780, filed Mar. 27, 1991 now U.S. Pat. No. 5,151,438, issued Sep. 29, 1992, which is a continuation-in-part of U.S. patent application Ser. No. 518,730, filed May 9, 1990 now U.S. Pat. No. 5,142,056, issued Aug. 25, 1992, which is a continuation-in-part of U.S. patent application Ser. No. 456,124, filed Dec. 22, 1989 now abandoned, which is a continuation-in-part of U.S. patent application Ser. No. 405,604, filed Sep. 8, 1989 now abandoned, which is a continuation-in-part of U.S. patent application Ser. No. 355,945, filed May 23, 1989 now abandoned.

TECHNICAL FIELD

The present invention relates to novel compounds and a composition and method for inhibiting retroviral proteases and in particular for inhibiting human immunodeficiency virus (HIV) protease, a composition and method for treating a retroviral infection and in particular an HIV infection, processes for making such compounds and synthetic intermediates employed in these processes.

BACKGROUND ART

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS) in man, hepatitis B virus, which causes hepatitis and hepatic carcinomas in man, human T-cell lymphotrophic viruses I, II, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. An inhibitor of a retroviral protease should provide a therapeutic agent for diseases caused by the retrovirus.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into core proteins, and also process the pol precursor into reverse transciptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for viral diseases usually involve administration of compounds that inhibit viral DNA synthesis. Current treatments for AIDS (Dagani, Chem. Eng. News, Nov. 23, 1987 pp. 41–49) involve administration of compounds such as 2',3'-dideoxycytidine, trisodium phosphonoformate, ammonium 21-tungsto-9-antimoniate, 1-beta-D-ribofuranosyl-1,2,4-triazole-3-carboxamide, 3'-azido-3'-deoxythymidine, and adriamycin that inhibit viral DNA synthesis; compounds such as AL-721 and polymannoacetate which may prevent HIV from penetrating the host cell; and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

DISCLOSURE OF THE INVENTION

In accordance with the present invention, there are retroviral protease inhibiting compounds of the formula:

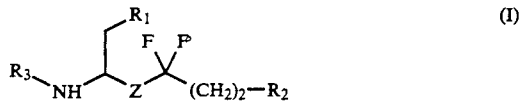

(I)

wherein $R_1$ is loweralkyl, cycloalkyl, phenyl or substituted derivatives thereof wherein the loweralkyl, cycloalkyl or phenyl group is substituted with one or two substituents independently selected from hydroxy, alkoxy, thioalkoxy and halo;

$R_2$ is phenyl, aromatic heterocyclic or substituted phenyl wherein the phenyl ring is substituted with one or two substituents independently selected from hydroxy, alkoxy, thioalkoxy and halo;

$R_3$ is

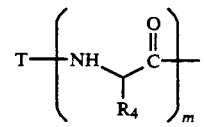

wherein m is 0 to 3 and $R_4$ is independently selected at each occurrence from hydrogen, loweralkyl, cycloalkylalkyl, haloalkyl, hydroxyalkyl, alkoxyalkyl, thioalkoxyalkyl, aminoalkyl, alkylaminoalkyl, dialkylaminoalkyl, carboxyalkyl, alkoxycarbonylalkyl and aminocarbonylalkyl and T is

wherein $R_6$ is aryl, heterocyclic or substituted aryl wherein the aryl ring is substituted with one or two substituents independently selected from hydroxy, alkoxy, thioalkoxy and halo, V is O or S, W is $CH_2$, $-CH_2CH_2-$, $-CH=CH-$ or $-D-CH=CH-$ wherein D is O, S or NH and Y is absent, O, S or $N(R_7)$ wherein $R_7$ is hydrogen or loweralkyl; or T is $R_{15}C(O)-$, $R_{15}C(S)-$ or $R_{15}S(O)_2-$ wherein $R_{15}$ is loweralkyl, aryl or heterocyclic; and Z is $-C(O)-$ or $-CH(OH)-$; or a pharmaceutically acceptable salt thereof; with the proviso that the compound is other than 5-(N-benzyloxycarbonyl-isoleucyl)-amino-3,3-difluoro-1,6-diphenyl-4-oxo-hexane.

The compounds of this invention having one asymmetric carbon atom can exist as the pure enantiomers or as the racemic mixture. The compounds of this invention having two or more asymmetric carbon atoms can exist as pure diastereomers, mixtures of diastereomers, diastereomeric racemates or mixtures of diastereomeric racemates. The present invention includes within its scope all of the isomeric forms. The terms "S" and "R" configuration as used herein are as defined by the IUPAC 1974 Recommendations for Section E, Fundamental Stereochemistry, Pure Appl. Chem. (1976) 45, 13–30.

The terms "Gly" and "Val" as used herein refer to glycine and valine, respectively. In general, the amino acid abbreviations used herein follow the IUPAC-IUB Joint Commission on Biochemical Nomenclature for amino acids and peptides (Eur. J. Biochem. 1984, 158, 9–31).

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "cycloalkyl" as used herein refers to an aliphatic ring having 3 to 7 carbon atoms including, but not limited to, cyclopropyl, cyclopentyl, cyclohexyl and the like.

The term "aryl" as used herein refers to a monocyclic or bicyclic carbocyclic ring system having one or more aromatic rings including, but not limited to, phenyl, naphthyl, tetrahydronaphthyl, indanyl and the like.

The term "arylalkyl" as used herein refers to an aryl group appended to a loweralkyl radical including, but not limited to, benzyl, 1-naphthylmethyl and the like.

The term "alkylamino" as used herein refers to a loweralkyl radical appended to an NH radical.

The term "dialkylamino" as used herein refers to $-NR_{30}R_{31}$ wherein $R_{30}$ and $R_3$ are independently selected from loweralkyl groups.

The term "heterocyclic ring" or "heterocyclic" as used herein refers to any 3- or 4-membered ring containing a heteroatom selected from oxygen, nitrogen and sulfur; or a 5- or 6-membered ring containing one, two or three nitrogen atoms; one nitrogen and one sulfur atom; or one nitrogen and one oxygen atom. The 5-membered ring has 0-2 double bonds and the 6-membered ring has 0-3 double bonds. The nitrogen heteroatoms can be optionally quaternized. The term "heterocyclic also includes bicyclic groups in which any of the above heterocyclic rings is fused to a benzene ring or a cyclohexane ring or another heterocyclic ring. Heterocyclics include: pyrrolyl, pyrrolinyl, pyrrolidinyl, pyrazolyl, pyrazolinyl, pyrazolidinyl, imidazolyl, imidalinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Heterocyclics can be unsubstituted or monosubstituted or disubstituted with substituents independently selected from hydroxy, halo, oxo (=O), alkylimino ($R*N=$ wherein $R*$ is a loweralkyl group), amino, alkylamino, dialkylamino, alkoxy, polyalkoxy, haloalkyl, cycloalkyl, aryl, arylalkyl, $-COOH$, $-SO_3H$ and loweralkyl. In addition, nitrogen containing heterocycles can be N-protected.

The term "halo" or "halogen" as used herein refers to $-Cl$, $-Br$, I or $-F$.

The terms "alkoxy" and "thioalkoxy" as used herein refer to $R_{32}O-$ and $R_{32}S-$, respectively, wherein $R_{32}$ is a loweralkyl group or benzyl.

The term "polyalkoxy" as used herein refers to $-OR_{33}$ wherein $R_{33}$ is a straight or branched chain containing 1-5, $C_{n'}-O-_{n''}$ linkages wherein n' and n'' are independently selected from 1 to 3, including but not limited to methoxyethoxymethoxy, methoxymethoxy and the like.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The term "cycloalkylalkyl" as used herein refers to a loweralkyl radical to which is appended a cycloalkyl group including, but not limited to, cyclohexylmethyl and the like.

The term "hydroxyalkyl" as used herein refers to a loweralkyl radical to which is appended a hydroxy group ($-OH$).

The term "alkoxyalkyl" as used herein refers to a loweralkyl radical to which is appended an alkoxy group.

The term "thioalkoxyalkyl" as used herein refers to a loweralkyl radical to which is appended an alkoxy group.

The term "aminoalkyl" as used herein refers to a loweralkyl radical to which is appended an amino group ($-NH_2$).

The term "alkylaminoalkyl" as used herein refers to a loweralkyl radical to which is appended an alkylamino group (i.e., $R_{40}NH-$ wherein $R_{40}$ is loweralkyl).

The term "dialkylaminoalkyl" as used herein refers to a loweralkyl radical to which is appended a dialkylamino group (i.e., $R_{41}R_{42}N-$ wherein $R_{41}$ and $R_{43}$ are independently selected from loweralkyl).

The term "carboxyalkyl" as used herein refers to a loweralkyl radical to which is appended a carboxyl group ($-COOH$).

The term "alkoxycarbonylalkyl" as used herein refers to a loweralkyl radical to which is appended an alkoxycarbonyl group (i.e., $R_{43}OC(O)-$ wherein $R_{43}$ is loweralkyl).

The term "aminocarbonylalkyl" as used herein refers to a loweralkyl radical to which is appended an aminocarbonyl group (i.e., —C(O)NH$_2$).

The term "N-protected" or "N-protecting group" as used herein refers to those groups intended to protect the N-terminus of an amino acid or peptide or to protect an amino group against undesirable reactions during synthetic procedures. N-protecting groups comprise carbamates, amides, N-alkyl derivatives, amino acetal derivatives, N-benzyl derivatives, imine derivatives, enamine derivatives and N-heteroatom derivatives, all of which are disclosed in Greene, "Protective Groups In Organic Synthesis," John Wiley & Sons, New York (1981), which is incorporated by reference herein. In particular, N-protecting groups include formyl, benzoyl, pivaloyl, benzyl, phenylsulfonyl, t-butyloxycarbonyl (Boc), benzyloxycarbonyl (Cbz) and the like.

Representative compounds of the invention include;

5(S)-(N-(2-Pyridyl)-methoxycarbonyl-(L)-valinyl)-amino-3,3-difluoro-1,6-diphenyl-4-oxo-hexane;

5(S)-(N-(2-Pyridyl)-methylamino-carbonyl-(L)-Valinyl)-amino-3,3-difluoro-1,6-diphenyl-4-oxo-hexane;

5(S)-(N-benzyloxycarbonyl-(L)-asparaginyl)-amino-3,3-difluoro-1,6-diphenyl-4-oxo-hexane;

5(S)-(N-Benzyloxycarbonyl-glycyl-(L)-valinyl)-amino-3,3-difluoro-1,6-diphenyl-4-oxo-hexane;

5(S)-(N-(2-pyridyl)methoxycarbonyl-glycyl-(L)-valinyl)-amino-3,3-difluoro-1,6-diphenyl-4-oxo-hexane;

5(S)-(N-(3-pyridyl)methoxycarbonyl-glycyl-(L)-valinyl)-amino-3,3-difluoro-1,6-diphenyl-4-oxo-hexane;

5(S)-(N-(4-pyridyl)methoxycarbonyl-glycyl-(L)-valinyl)-amino-3,3-difluoro-1,6-diphenyl-4-oxo-hexane;

5(S)-(N-(2-pyridylmethyl)aminocarbonyl-glycyl-(L)-valinyl)-amino-3,3-difluoro-1,6-diphenyl-4-oxo-hexane;

5(S)-(N-(3-pyridylmethyl)aminocarbonyl-glycyl-(L)-valinyl)-amino-3,3-difluoro-1,6-diphenyl-4-oxo-hexane;

5(S)-(N-(4-pyridylmethyl)aminocarbonyl-glycyl-(L)-valinyl)-amino-3,3-difluoro-1,6-diphenyl-4-oxo-hexane;

5(S)-(N-(2-pyridylmethyl)-N-(methyl)aminocarbonyl-glycyl-(L)-valinyl)-amino-3,3-difluoro-1,6-diphenyl-4-oxo-hexane;

5(S)-(N-(3-pyridylmethyl)-N-(methyl)aminocarbonyl-glycyl-(L)-valinyl)-amino-3,3-difluoro-1,6-diphenyl-4-oxo-hexane;

5(S)-(N-(4-pyridylmethyl)-N-(methyl)aminocarbonyl-glycyl-(L)-valinyl)-amino-3,3-difluoro-1,6-diphenyl-4-oxo-hexane;

5(S)-(N-(2-(2-Pyridyl)ethanesulfonyl)-glycyl-(L)-valinyl)-amino-3,3-difluoro-1,6-diphenyl-4-oxohexane;

5(S)-(N-Acetylglycyl-(L)-valinyl)-amino-3,3-difluoro-1,6-diphenyl-4-oxo-hexane; and 5(S)-(N-(Methanesulfonyl)-glycyl-(L)-valinyl)-amino-3,3-difluoro-1,6-diphenyl-4-oxo-hexane.

The compounds of the invention can be prepared as outlined in the processes shown in Schemes I and II. According to Scheme 1, oxazolidinone 1 (wherein $R_1$ is defined as above and $R_{10}$ is an activating group, such as —N(OCH$_3$)(CH$_3$) and the like) is reacted with an organometallic reagent R$_2$CH$_2$M (2) (wherein R$_2$ is defined as above and M is a metal ion, for example, R$_2$CH$_2$Li, R$_2$CH$_2$MgCl and the like). Oxazolidinone 1 can be prepared according to the procedure disclosed in European Patent Application No. EP402646, published Dec. 19, 1990 (U.S. patent application Ser. No. 518,730, filed May 9, 1990, which is incorporated by reference herein). Difluoroketone 3 is then converted to 4 (for example, by reduction to the alcohol, formation of the mesylate, elimination to the olefin and hydrogenation). Deprotection of 4 (for example, by treatment with barium hydroxide and the like), followed by coupling with carboxylic acid 5, or an activated derivative thereof, provides difluoroalcohol 6a. Oxidation of 6a (for example, with Na$_2$Cr$_2$O$_7$/acetic acid and the like) provides 6b.

Scheme II illustrates an alternative process for the preparation of the deprotected form of 4 (i.e., 12). N-protected amino alcohol 7 ($R_1$ is as defined above and $R_{20}$ is an N-protecting group, for example, t-butyloxycarbonyl) is oxidized (for example, by Swern oxidation) to provide aldehyde 8. Reaction of aldehyde 8 with substituted acetylene 9 ($R_2$ is defined as above) and zinc in an inert solvent provides difluoro alcohol 10. Hydrogenation of 10 gives 11, which can be deprotected to provide 12.

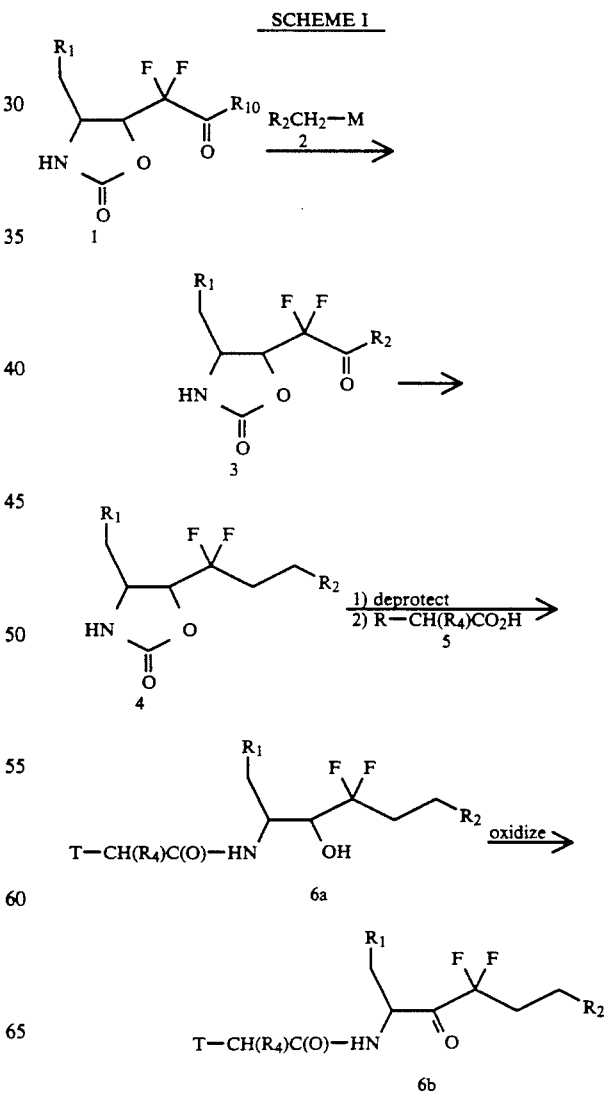

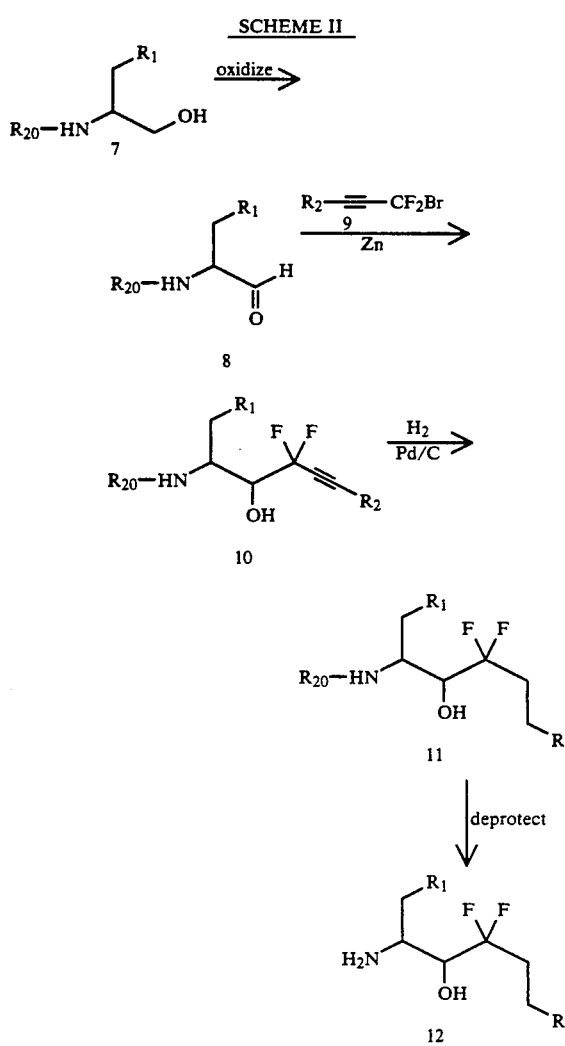

SCHEME II

Intermediates useful for the preparation of compounds I include compounds of the formula:

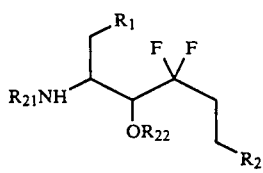

wherein $R_1$ is loweralkyl, cycloalkyl, phenyl or substituted derivatives thereof wherein the loweralkyl, cycloalkyl or phenyl group is substituted with one or two substituents independently selected from hydroxy, alkoxy, thioalkoxy and halo;

$R_2$ is phenyl, aromatic heterocyclic or substituted phenyl wherein the phenyl ring is substituted with one or two substituents independently selected from hydroxy, alkoxy, thioalkoxy and halo;

$R_{21}$ is hydrogen or an N-protecting group; and $R_{22}$ is hydrogen, or $R_{21}$ and $R_{22}$ taken together are —C(O)—.

Other useful intermediates for the preparation of compounds I include compounds of the formula:

$$T\text{—}(NHCH(R_4)C(O))_m\text{—}OH$$

wherein m is 0 to 3 and $R_4$ is independently selected at each occurrence from hydrogen, loweralkyl, cycloalkylalkyl, haloalkyl, hydroxyalkyl, alkoxyalkyl, thioalkoxyalkyl, aminoalkyl, alkylaminoalkyl, dialkylaminoalkyl, carboxyalkyl, alkoxycarbonylalkyl and aminocarbonylalkyl and T is

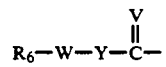

wherein $R_6$ is aryl, heterocyclic or substituted aryl wherein the aryl ring is substituted with one or two substituents independently selected from hydroxy, alkoxy, thioalkoxy and halo, V is O or S, W is $CH_2$, —$CH_2CH_2$—, —CH=CH— or —D—CH=CH— wherein D is O, S or NH and Y is absent, O, S or $N(R_7)$ wherein $R_7$ is hydrogen or loweralkyl; or T is $R_{15}C(O)$—, $R_{15}C(S)$— or $R_{15}S(O)_2$— wherein $R_{15}$ is loweralkyl, aryl or heterocyclic; or an acid halide or activated ester derivative thereof.

Acid halide derivatives of the above intermediates include the acid chloride. Activated ester derivatives of the above intermediates include activated esters commonly used by those skilled in the art for activating carboxylic acid groups for coupling with an amine to form a peptide bond including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 4-nitrophenol derived esters, 2,4,5-trichlorophenol derived esters and the like.

The following examples will serve to further illustrate the preparation of the novel compounds of the invention.

EXAMPLE 1

5(S)-(N-Benzyloxycarbonyl-(L)-valinyl)-amino-1-(2-pyridyl)-6-phenyl-3,3-difluoro-4-oxo-hexane

1A.

4(S)-Benzyl-5(R)-(2'-(2',2'-difluoro-N'-methoxy-N'-methylcetamido)-2-oxazolidinone To a solution of 1.36 g of the 2-oxazolidinone derivative of 4(S)-amino-5-phenyl-2,2-difluoro-3(R)-hydroxypentanoic acid (European Patent Application No. EP402646, published Dec. 19, 1990) in 20 ml of dimethylformamide (DMF) was added successively, 615 mg of N,O-dimethyl hydroxylamine hydrochloride, 2.11 ml of triethylamine and 1.47 g of 1-(3-dimethylaminopropyl)-3-ethyl carbodiimide hydrochloride. The reaction mixture was stirred at room temperature overnight. The solvent was removed in vacuo and the residue was extracted with ethyl acetate and washed successively with saturated aqueous sodium carbonate and saturated aqueous sodium chloride, then dried and concentrated. Silica gel chromatography (20% ethyl acetate/methylene chloride) provided 1.3 g of the desired product. $^1$H NMR (CDCl$_3$): δ 2.85 (m, 2H), 3.10 (m, 2H), 3.20 (s, 3H), 3.73 (s, 3H), 4.10 (m, 1H), 4.90 (m, 1H), 5.10 (br s, 1H), 7.25 (m, 5H).

1B.
4(S)-Benzyl-5(R)-(3'-(3',3'-difluoro-2'-oxo-1'-(2-pyridyl)propyl))-2-oxazolidinone To 500 mg of the product from Example 1A in 10 ml of tetrahydrofuran (THF) at −78° C. was added a solution of the lithium derivative of 2-picoline (generated by adding 2.5 ml of a 1.6 M solution of n-BuLi in hexane to 0.39 ml of 2-picoline in 5 ml of THF at −78° C.). After stirring for 30 minutes at −78° C., and then for 30 minutes at −10° C., the reaction mixture was quenched by adding saturated aqueous ammonium chloride solution. This mixture was then extracted with ethyl acetate. The combined organic layer was dried and concentrated. Silica gel chromatography (2–5% methanol/methylene chloride) provided 405 mg of the desired product. $^1$H NMR (CDCl$_3$): δ 2.80 (m, 1H), 3.05 (m, 1H), 4.30 (m, 1H), 4.85 (m, 1H), 5.0 (br s, 1H), 5.90 (s, 1H), 7.05–7.30 (m, 7H), 7.70 (m, 1H), 8.05 (d, 1H).

1C.
5(S)-amino-1-(2-pyridyl)-6-phenyl-3.3-difluoro-4(R)-hydroxyhexane

To 150 mg of the product from Example 1B in methanol at 0° C. was added a solution of 30 mg of sodium borohydride in 10 ml of methanol. After stirring for 30 minutes, the product was isolated. The crude product was treated with 1.1 equivalents of triethylamine and 1.0 equivalents of methanesulfonyl chloride in methylene chloride to provide the mesylate derivative. The crude mesylate was treated with 5 equivalents of DBU in 5 ml of toluene at 80° C. to provide the olefin. The olefin was hydrogenated using 10% Pd/C as catalyst and methanol as solvent. The resulting product was hydrolyzed using barium hydroxide in 1:1 dioxane/water to provide the desired product. Mass spectrum: (M+1)=307.

1D.
5(S)-(N-Benzyloxycarbonyl-(L)-valinyl)-amino-1-(2-pyridyl-6-phenyl-3,3-difluoro-4-oxo-hexane To 100 mg of the resultant product of Example 1C in 5 ml of DMF was added successively, 100 mg of N-benzyloxycarbonyl-(L)-valine, 160 mg of HOBt, 0.117 ml of triethylamine and 160 mg of 1-(3-dimethylaminopropyl)-3-ethyl carbodiimide hydrochloride. The reaction mixture was stirred at room temperature overnight. The product was isolated and purified by silica gel chromatography (2% methanol/methylene chloride) to provide 145 mg of the crude alcohol, which was oxidized by dissolving in 5 ml of acetic acid and adding 1.1 equivalents of sodium dichromate (Synthesis, 466(1989)), resulting in the desired product. $^1$H NMR (CDCl$_3$): δ 0.81 (d, 3H), 0.90 (d, 3H), 2.05 (m, 1H), 2.50–3.30 (m, 6H), 3.95 (m, 1H), 5.05 (s, 2H), 5.20 (br d, 1H), 5.30 (m, 1H), 6.30 (br d, 1H), 7.10–7.35 (m, 7H), 7.60 (m, 1H), 8.50 (m, 1H). Mass spectrum: (M+1)=538.

EXAMPLE 2
5(S)-(N-(2-Pyridyl)-methoxycarbonyl-(L)-valinyl)-amino-3,3-difluoro-1,6-diphenyl-4-oxo-hexane 4(S)-Benzyl-5(R)-(3'-(3,3'-difluoro-1'-phenylpropyl)-2-oxazolidinone (European Patent Application No. EP402646, published Dec. 19, 1990) was deprotected by treatment with barium hydroxide. The resultant difluoroamino alcohol was coupled to 5-(N-(2 -pyridyl)-methoxycarbonyl)valine using N-ethyl-N'-(dimethylaminopropyl)carbodiimide, 1-hydroxybenzotriazole and trimethylamine in dimethylformamide (DMF). Oxidation of the resultant compound according to Example 1D using sodium dichromate in acetic acid provided the desired compound (65%). $^1$H NMR (CDCl$_3$): δ 0.82 (d, 3H), 0.90 (d, 3H), 2.05 (m, 1H), 2.35 (m, 2H), 2.80–2.95 (m, 2H), 3.30 (m, 1H), 3.95 (q, 1H), 5.20 (s, 2H), 5.30 (m, 1H), 6.20 (brd, 1H), 7.10–7.30 (m, 12H), 7.70 (t, 1H), 8.60 (d, 1H).

EXAMPLE 3
5(S)-(N-(2-Pyridyl)-methylamino-carbonyl-(L)-Valinyl)-amino-3,3-difluoro-1.6-diphenyl-4-oxo-hexane Using the procedure of Example 2, but replacing 5-(N-(2-pyridyl)-methoxycarbonyl)-valine with 5-(N-(2-pyridyl)-methylamino-carbonyl)-Valine provided the desired compound. $^1$H NMR (CDCl$_3$): δ 0.82 (d, 3H), 0.90 (d, 3H), 2.07 (m, 1H), 2.30 (m, 1H), 2.80–3.30 (m, 4H), 4.10 (q, 1H), 4.45 (d, 1H), 5.30 (m, 1H), 5.55 (t, 1H), 6.50 (d, 1H), 7.12–7.30 (m, 12H), 7.65 (m, 1H), 8.50 (m, 1H).

EXAMPLE 4
5(S)-(N-Benzyloxycarbonyl-glycyl-(L)-Valinyl)-amino-3,3-difluoro-1,6-diphenyl-4-oxo-hexane Using the procedure in Example 2, but replacing 5-(N-(2-pyridyl)methoxycarbonyl)-valine with 5-N-Cbz-glycylvaline provided the desired product. $^1$H NMR (CDCl$_3$): δ 0.80 (d, 3H), 0.88 (d, 3H), 2.05 (m, 1H), 2.40 (m, 2H), 2.70–3.30 (m, 4H), 3.70 (m, 2H), 4.20 (q, 1H), 5.10 (s, 2H), 5.30 (m, 1H), 6.30 (m, 2H), 7.12–7.38 (m, 15H).

EXAMPLE 5
N-t-Butyloxycarbonyl-(1,6-diphenyl-3,3-difluoro-4(R,S)-hydroxy-5(S)-amino-hexyne To a solution of 1 gm of Boc-phenylalaninal in 12 ml of THF was added 1.05 gm of zinc dust and 0.16 gm of mercuric chloride. To this sonicated suspension was added a solution of 0.25 gm of bromodifluoromethylphenylacetylene in 4 ml of THF over a one hour period. Excess zinc was filtered and the filtrate concentrated and washed with 10% aq. KHSO$_4$ solution. Extraction with EtOAc (3×100 ml), drying with anhydrous Na$_2$SO$_4$ and evaporation of the solvent in vacuo provided a yellow oil which was purified by silica gel column chromatographyto give 1.09 gm of the desired product (68%). Mass spectrum: (M +1) =402. $^1$H NMR (CDCl$_3$): δ 1.34 (s, 9H), 2.95–3.20 (m, 2H), 3.90–4.10 (m, 2H), 5.05 (br d, 1H), 7.25–7.50 (m, 10H).

EXAMPLE 6
N-t-butyloxycarbonyl-(1,6-diphenyl-3,3-difluoro-4(R,S)-hydroxy-5(S)-amino-hexane)

To a suspension of 21 mg of 10% palladium on carbon was added a methanol solution of the resultant product from Example 5. The suspension was stirred vigorously under a hydrogen atmosphere. After one hour, the catalyst was filtered off and the filtrate concentrated to provide 81 mg (95%) of desired product. Mass spectrum: (M+1)=406. $^1$H NMR (CDCl$_3$): δ 1.40 (s, 9H), 2.25 (m, 2H), 2.70–3.10 (m, 4H), 3.50 (m, 1H), 3.70 (m, 1H), 4.0 (m, 1H), 4.90 (br d, 1H), 7.25 (m, 10H).

EXAMPLE 7

1,6-Diphenyl-3,3-difluoro-4(R,S)-hydroxy-5(S)amino-hexane

To 1 gm of the resultant product from Example 6 was added 5 ml of trifluoroacetic acid and 5 ml of dichloromethane. After one hour at room temperature, the solution was concentrated to an oil. The oil was dissolved in 100 ml EtOAc and washed with saturated NaHCO$_3$ solution. The organic layer was dried with anhydrous Na$_2$SO$_4$ and evaporation of the solvent in vacuo provided a white solid, 740 mg (98%). Mass spectrum: (M+1)=306.

EXAMPLE 8

5(S)-(N-(2-(2-Pyridyl)ethanefulfonyl)-glycyl-(L)-valinyl)-amino-3,3-difluoro-1,6-diphenyl-4-oxohexane Coupling of N-(2-(2-pyridyl)ethanesulfonyl)glycyl-valine to the resultant product from Example 7 using the procedure of Example 2, followed by oxidation with sodium dichromate in acetic acid provided the desired product. Mass spectrum: (M+1) =629. $^1$H NMR (CDCl$_3$): δ 0.75 (d, 3H), 0.85 (d, 3H), 2.10 (m, 1H), 2.40 (m, 2H), 2.80 (m, 3H), 3.30 (m, 3H), 3.60 (m, H), 3.68 (br d, 2H), 4.20 (m, 1H), 5.30 (m, 1H), 5.95 (m, 1H), 6.60 (d, 1H), 6.80 (d, 1H), 7.20 (m, 2H), 7.60 (m, 1H), 8.50 (d, 1H).

EXAMPLE 9

5(S)-(N-Acetylglycyl-(L)-valinyl)-amino-3,3-difluoro-1,6-diphenyl-4-oxo-hexane Using the procedure described in Example 8, but replacing N-(2-(2-pyridylethane)sulfonyl)glycyl-valine with N-acetyl-glycyl-valine provided the desired product. Mass spectrum: (M+1)=502. $^1$H NMR (CDCl$_3$): δ 0.80 (d, 3H), 0.88 (d, H), 2.03 (s, 3H), 2.02 (m, 1H), 2.45 (m, 2H), 2.80 (t, 2H), 2.92 (m, 1H), 3.30 (m, 1H), 3.89 (m, 2H), 4.20 (m, 1H), 5.30 (m, 1H), 6.20 (m, 1H), 6.40 (t, 2H), 7.25 (m, 10H).

EXAMPLE 10

5(S)-(N-(Methanesulfonyl)-glycyl-(L)-valinyl)amino-3,3-difluoro-1,6-diphenyl-4-oxo-hexane Using the procedure described in Example 8, but replacing N-(2-(2-pyridyl)ethanesulfonyl)-glycyl-valine with N-(methanesulfonyl)-glycyl-valine provided the desired product. Mass spectrum: (M+1)=538. $^1$H NMR (CDCl$_3$): 0.81 (d, 3H), 0.88 (d, 3H), 2.05 (m, 1H), 2.35 (m, 2H), 2.85 (m, 3H), 2.95 (s, 3H), 3.30 (dd, 1H), 3.80 (d, 2H), 4.20 (m, 1H), 5.20 (m, 1H), 5.30 (m, 1H), 6.30 (d, 1H), 6.55 (d, 1H), 7.25 (m, 10H).

EXAMPLE 11

Using the methods outlined above, the following compounds can be prepared:
(a) 5-(N-benzyloxycarbonyl-(L)-isoleucyl)-amino-3,3-difluoro-1,6-diphenyl-4-oxo-hexane;
(b) 5-(N-benzyloxycarbonyl-(L)-tert-leucyl)-amino-3,3-difluoro-1,6-diphenyl-4-oxo-hexane;
(c) 5-(N-benzyloxycarbonyl-(L)-asparaginyl)-amino-3,3-difluoro-1,6-diphenyl-4-oxo-hexane;
(d) 5(S)-(N-(2-pyridyl)methoxycarbonyl-glycyl-(L)-valinyl)-amino-3,3-difluoro-1,6-diphenyl-4-oxo-hexane;
(e) 5(S)-(N-(3-pyridyl)methoxycarbonyl-glycyl-(L)-valinyl)-amino-3,3-difluoro-1,6-diphenyl-4-oxo-hexane;
(f) 5(S)-(N-(4-pyridyl)methoxycarbonyl-glycyl-(L)-valinyl)-amino-3,3-difluoro-1,6-diphenyl-4-oxo-hexane;
(g) 5(S)-(N-(2-pyridylmethyl)aminocarbonyl-glycyl-(L)-valinyl)-amino-3,3-difluoro-1,6-diphenyl-4-oxohexane;
(h) 5(S)-(N-(3-pyridylmethyl)aminocarbonyl-glycyl-(L)-valinyl)-amino-3,3-difluoro-1,6-diphenyl-4-oxohexane;
(i) 5(S)-(N-(4-pyridylmethyl)aminocarbonyl-glycyl-(L)-valinyl)-amino-3,3-difluoro-1,6-diphenyl-4-oxohexane;
(j) 5(S)-(N-(2-pyridylmethyl)-N-(methyl)aminocarbonylglycyl-(L)-valinyl)-amino-3,3-difluoro-1,6-diphenyl-4-oxohexane;
(k) 5(S)-(N-(3-pyridylmethyl)-N-(methyl)aminocarbonylglycyl-(L)-valinyl)-amino-3,3-difluoro-1,6-diphenyl-4-oxohexane; and
(l) 5(S)-(N-(4-pyridylmethyl)-N-(methyl)aminocarbonylglycyl-(L)-valinyl)-amino-3,3-difluoro-1,6-diphenyl-4-oxohexane.

Fluorogenic Assay for Screening Inhibitors of HIV

The inhibitory potency of the compounds of the invention can be determined by the following method.

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1 M sodium chloride, 5 mM dithiothreitol, 0.5 mg/ml bovine serum albumin, 1.3 μM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmision 490 nM) is recorded as a function of time. The reaction rate is determined for the first six to eight minutes. The observed rate is directly proportional to the moles of substrate cleaved per unit time. The IC$_{50}$ is the concentration of test compound needed to inhibit the protease by 50%.

Fluorogenic substrate: Dabcyl-Ser-Gln-Asn-Tyr-Pro-Ile-Val-Gln-EDANS wherein DABCYL=4-(4-dimethylaminophenyl)azobenzoic acid and EDANS=5-((2-aminoethyl)amino)naphthalene-1-sulfonic acid.

Table 1 shows the inhibitory potencies of compounds of the invention against HIV-1 protease.

TABLE 1

| Compound of Example | IC$_{50}$ (nM) |
| --- | --- |
| 1 | 14 |
| 2 | 2.2 |
| 3 | 2.9 |
| 4 | 1.0 |
| 8 | 2.5 |
| 9 | 3.2 |
| 10 | 2.2 |
| 11c | 21 |

The results indicate that the compounds are effective as inhibitors of HIV-1 protease.

Antiviral Activity

The anti-HIV activity of the compounds of the invention can be determined in MT4 cells according to the procedure of Pauwels et. al. (*J. Virol. Methods* 1988, 20, 309). The $IC_{50}$ is the concentration of compound that gives 50% inhibition of the cytopathic effect of HIV. The $LC_{50}$ is the concentration of compound at which 50% of the cells remain viable.

Table 2 shows the inhibitory potencies of compounds of the invention against HIV-1$_{3B}$ in MT4 cells.

TABLE 2

| Compound of Example | $IC_{50}$ ($\mu M$) | $LC_{50}$ ($\mu M$) |
| --- | --- | --- |
| 1 | 5.7 | >100 |
| 2 | 6.3 | 21 |
| 3 | 7.6 | >100 |
| 4 | 1.9 | >100 |
| 8 | 4.9 | >100 |
| 9 | 8.6 | >100 |
| 10 | 4.3 | >100 |
| 11c | 10.4 | >100 |

The results indicate that the compounds are effective as inhibitors of the cytopathic effect of HIV in cell culture.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, omides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the invention are useful for inhibiting a retroviral protease, in particular HIV protease, in vitro or in vivo. The compounds of the present invention are also useful for the treatment or prophylaxis of diseases caused by retroviruses, especially acquired immune deficiency syndrome or an HIV infection in a human or other mammal.

Total daily dose administered to a host in single or divided doses may be in amounts, for example, from 0.001 to 100 mg/kg body weight daily and more usually 0.1 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

While a compound of the invention can be administered as the sole active pharmaceutical agent, they can also be used in combination with one or more immunomodulators, antiviral agents, other antiinfective agents or vaccines. Other antiviral agents to be administered in combination with a compound of the present invention include AL-721, beta interferon, polymannoacetate, ganciclovir, dideoxycytidine, trisodium phosphonoformate, HPA-23, eflonithine, Peptide T, Reticulose (nucleophosphoprotein), zidovudine (AZT), ansamycin LM 427, trimetrexate, UA001, ribavirin, alpha interferon, oxetanocin, DDC, DDI, cylobut G and acyclovir. Immunomodulators that can be administered in combination with a compound of the present invention include bropirimine, Ampligen, anti-human alpha interferon antibody, colony stimulating factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone and tumor necrosis factor. Other antiinfective agents that can be administered in combination with a compound of the present invention include pentamidine isethionate. Any of a variety of HIV or AIDS vaccines can be used in combination with a compound of the present invention.

It will be understood that agents which can be combined with the compounds of the present invention for the treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

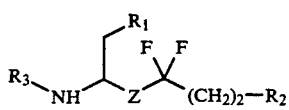

wherein $R_1$ is loweralkyl, cycloalkyl, phenyl, substituted loweralkyl, substituted cycloalkyl or substituted phenyl wherein the loweralkyl, cycloalkyl or phenyl group is substituted with one or two substituents independently selected from group is substituted with one or two substituents independently selected from hydroxy, alkoxy, thioalkoxy and halo;

$R_2$ is phenyl or substituted phenyl wherein the phenyl ring is substituted with one or two substituents independently selected from hydroxy, alkoxy, thioalkoxy and halo;

$R_3$ is

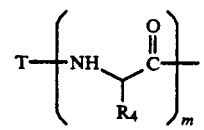

wherein m is 1 and $R_4$ is hydrogen, loweralkyl, cycloalkylalkyl, haloalkyl, hydroxyalkyl, alkoxyalkyl, thioalkoxyalkyl, aminoalkyl, alkylaminoalkyl, dialkylaminoalkyl, carboxyalkyl, alkoxycarbonylalkyl or aminocarbonylalkyl and T is

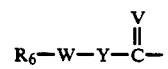

wherein $R_6$ is pyridyl or substituted pyridyl wherein the pyridyl ring is substituted with one or two substituents independently selected from hydroxy, alkoxy, amino, alkylamino, dialkylamino, polalkoxy, haloalkyl, cycloalkyl, aryl, arylalkyl, —COOH, —SO$_3$H, loweralkyl and halo, V is O or S, W is CH$_2$, —CH$_2$CH$_2$—, —CH=CH— or —D—CH=CH— wherein D is O, S or NH and Y is absent, O, S or N($R_7$) wherein $R_7$ is hydrogen or loweralkyl; and Z is —C(O)— or —CH(OH)—; or a pharmaceutically acceptable salt thereof; wherein the term aryl as used herein refers to phenyl, naphthyl, tetrahydronaphthyl or indanyl.

2. The compound of claim 1 wherein $R_1$ is phenyl; $R_2$ is phenyl $R_4$ is loweralkyl; and Z is —C(O)—.

3. The compound of claim 1 wherein T is N-(2-pyridylmethyl)aminocarbonyl, N-(3-pyridylmethyl)aminocarbonyl, N-(4-pyridyl-methyl)aminocarbonyl, 2-pyridylmethoxycarbonyl, 3-pyridylmethoxycarbonyl, 4-pyridylmethoxycarbonyl, N-(2-pyridylmethyl)-N-(methyl)-aminocarbonyl, N-(3-pyridylmethyl)-N-(methyl)-aminocarbonyl or N-(4-pyridylmethyl)-N-(methyl)-aminocarbonyl.

4. A compound of the formula:

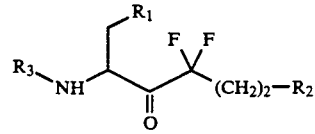

wherein $R_1$ is phenyl;
$R_2$ is phenyl;
$R_3$ is

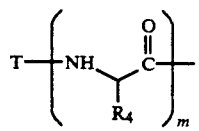

wherein m is 1, R₄ is loweralkyl and T is

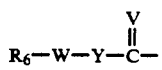

wherein $R_6$ is pyridyl or substituted pyridyl wherein the pyridyl ring is substituted with one or two substituents independently selected from hydroxy, alkoxy, amino, alkylamino, dialkylamino, polalkoxy, haloalkyl, cycloalkyl, aryl, arylalkyl, —COOH, —SO₃H, loweralkyl and halo, V is O or S, W is CH₂, —CH₂CH₂—, —CH=CH— or —D—CH=CH— wherein D is O, S or NH and Y is absent, O, S or N($R_7$) wherein $R_7$ is hydrogen or loweralkyl; or a pharmaceutically acceptable salt thereof; wherein the term aryl as used herein refers to phenyl, naphthyl, tetrahydronaphthyl or indanyl.

5. The compound of claim 4 wherein R₄ is isopropyl.

6. The compound of claim 1 wherein T is N-(2-pyridylmethyl)aminocarbonyl, N-(3-pyridylmethyl)aminocarbonyl, N-(4-pyridyl-methyl)aminocarbonyl, 2-pyridylmethoxycarbonyl, 3-pyridylmethoxycarbonyl, 4-pyridylmethoxycarbonyl, N-(2-pyridylmethyl)-N-(methyl)-aminocarbonyl, N-(3-pyridylmethyl)-N-(methyl)-aminocarbonyl or N-(4-pyridylmethyl)-N-(methyl)-aminocarbonyl.

7. A compound of the formula:

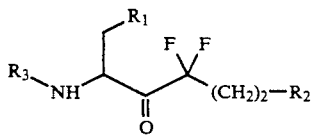

wherein R₁ is phenyl;
R₂ is phenyl;
R₃ is

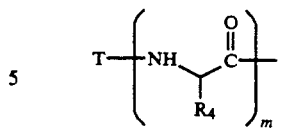

wherein m is 1, R₄ is isopropyl and T is

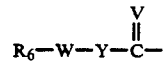

wherein $R_6$ is pyridyl, V is O or S, W is CH₂ or —CH₂CH₂— and Y is O, S or N($R_7$) wherein $R_7$ is hydrogen or loweralkyl; or a pharmaceutically acceptable salt thereof.

8. The compound of claim 7 wherein T is N-(2-pyridylmethyl)aminocarbonyl, N-(3-pyridylmethyl)aminocarbonyl, N-(4-pyridyl-methyl)aminocarbonyl, 2-pyridylmethoxycarbonyl, 3-pyridylmethoxycarbonyl, 4-pyridylmethoxycarbonyl, N-(2-pyridylmethyl)-N-(methyl)-aminocarbonyl, N-(3-pyridylmethyl)-N-(methyl)-aminocarbonyl or N-(4-pyridylmethyl)-N-(methyl)-aminocarbonyl.

9. A compound selected from the group consisting of: 5(S)-(N-(2-Pyridyl)-methoxycaronbyl-(L)-valinyl)-amino-3,3-difluoro-1,6-diphenyl-4-oxo-hexane and 5(S)-(N-(2-Pyridyl)-methylamino-carbonyl-(L)-Valinyl)-amino-3,3-difluoro-1,6-diphenyl-4-oxo-hexane; or a pharmaceutically acceptable salt thereof.

10. A method for inhibiting HIV protease comprising administering to a human in need of such treatment a therapeutically effective amount of a compound of claim 1.

11. A method for inhibiting HIV protease comprising administering to a human in need of such treatment a therapeutically effective amount of a compound of claim 4.

12. A method for inhibiting HIV protease comprising administering to a human in need of such treatment a therapeutically effective amount of a compound of claim 7.

13. A method for inhibiting HIV protease comprising administering to a human in need of such treatment a therapeutically effective amount of a compound of claim 9.

* * * * *

UNITED STATES PATENT AND TRADEMARK OFFICE
CERTIFICATE OF CORRECTION

PATENT NO. : 5,256,677
DATED : October 26, 1993
INVENTOR(S) : Hing L. Sham; Daniel W. Norbeck; Dale J. Kempf; Chen Zhao;

It is certified that error appears in the above-indentified patent and that said Letters Patent is hereby corrected as shown below:

COLUMN 16, LINE 34:  Delete "polalkoxy" and Insert --polyalkoxy--

COLUMN 17, LINE 20:  Delete "polalkoxy" and Insert --polyalkoxy--

COLUMN 17, LINE 30:  Delete "Claim 1" and Insert --Claim 4--.

COLUMN 18, LINE 29:  Delete "methoxycaronbyl" and Insert --methoxycarbonyl--.

Signed and Sealed this

Tenth Day of May, 1994

Attest:

BRUCE LEHMAN

*Attesting Officer*  *Commissioner of Patents and Trademarks*